United States Patent

Hakky et al.

[11] Patent Number: 5,312,399
[45] Date of Patent: May 17, 1994

[54] LASER RESECTOSCOPE WITH MECHANICAL CUTTING MEANS AND LASER COAGULATING MEANS

[76] Inventors: Said I. Hakky, 8547 Merrimoor Blvd., East, Largo, Fla. 34647-3145; Perry B. Hudson, 2225 Park St., North, St. Petersburg, Fla. 33710

[21] Appl. No.: 961,766

[22] Filed: Sep. 29, 1992

[51] Int. Cl.$^5$ .............................................. A61B 17/36
[52] U.S. Cl. ........................................ 606/15; 606/14; 606/16; 606/170
[58] Field of Search ............................... 128/749-758; 604/21, 22; 606/13-15, 127, 128, 170, 180

[56] References Cited

U.S. PATENT DOCUMENTS

| | | | |
|---|---|---|---|
| 4,469,098 | 9/1984 | Davi | 606/7 |
| 4,631,052 | 12/1986 | Kensey | 604/22 |
| 4,811,735 | 3/1989 | Nash et al. | 604/22 |
| 4,955,882 | 9/1990 | Hakky | 606/170 |

*Primary Examiner*—Stephen C. Pellegrino
*Assistant Examiner*—Michael Peffley

*Attorney, Agent, or Firm*—Caesar, Rivise, Bernstein, Cohen & Pokotilow, Ltd.

[57] ABSTRACT

A resectoscope and a method of use for removing organic tissue, e.g., the prostate gland, from the body of a living being. The resectoscope includes an elongated member having a distal end adapted to be introduced into the body of the being at the situs of organic tissue to be removed via a tubular sheath. The resectoscope includes a laser for producing a laser beam adjacent the distal end of the elongated member to penetrate several millimeters through the surface of the tissue to coagulate. A rotatable cutter, e.g., a pair of angled offset planar blades, is disposed at the distal end of the elongated member and is arranged to be rotated at a high rate of speed by an associated drive assembly to cut the coagulated tissue. A lumen is provided to carry an irrigation liquid to the situs of the tissue. A suction lumen is provided to carry the tissue removed by the cutter so that it can be retrieved for histological examination. A viewing system is also provided and extends through the resectoscope in order to enable the operator to view the lasing and cutting of the tissue.

48 Claims, 4 Drawing Sheets

LASER RESECTOSCOPE WITH MECHANICAL CUTTING MEANS AND LASER COAGULATING MEANS

FIELD OF THE INVENTION

This invention relates generally to the field of surgical devices and more particularly to resectoscopes and methods of use.

BACKGROUND OF THE INVENTION

A resectoscope is employed transurethrally to perform prostate and/or bladder surgery. This device has an elongate central working section provided with an outer sheath, usually made of stainless steel, which is inserted into the urethra. The outer sheath prevents the urethra from collapsing, while the working elements internally of the sheath are employed to cut away the desired tissue.

Until recently the treatment of benign prostate hyperplasia has been by use of a technique called transurethral resection of the prostate (TURP) utilizing conventional resectoscopes. Such resectoscopes for the most part either are of the cold punch type, wherein the cutting element is unheated, or are of the heated type, where the cutting element, in the form of a conductive wire, is heated through an electrical connection to a diathermy unit. The diathermy unit can be controlled by the surgeon, either through the use of a hand-operated switch or through the use of a foot-operated switch.

In a manually operated resectoscope of the type employing a heated cutting element, the surgeon manually extends the cutting element beyond the end of the outer sheath to a position engaging the tissue to be cut. Thereafter, the cutting element is energized through actuation of the diathermy unit, and at the same time the cutting element is manually retracted to cause it to slice away a desired amount of the tissue. The surgeon views the area being operated upon through a telescopic system that also is mounted within the stainless steel sheath of the device, and a continuous irrigation system is utilized to keep the line-of-sight free of blood and other debris.

During prostate surgery it is common to cut away approximately 1/10 of a gram of tissue with each cutting stroke of the resectoscope. Although the total weight of tissue to be removed varies with the size of the individual and the severity of the problem, it is quite common to remove anywhere from 20 to 150 grams of tissue in a typical prostate operation. Therefore, in even the simplest of operations, it is generally necessary to reciprocate the cutting element at least 200 times.

During transurethral resection of the prostate, fluids are used to irrigate the operative situs during the operation as well as during the immediate postoperative period. The fluid irrigation during the resection has two purposes: to first clarify the area so that the operator's vision is unobstructed and second to remove any prostatic chips toward the bladder. Therefore, the bladder acts as a temporary reservoir for prostatic chips and blood clots. Before the procedure is completed, and sometimes in the middle of the procedure, the bladder must be irrigated and cleared completely of any prostatic chips or clots. It would, however, facilitate the operation if irrigation fluid and the prostatic chips or clots could be removed without having to irrigate the bladder.

In the diathermy unit previously discussed, electricity is used both for cutting and coagulation. The electricity runs through a hot metal were (isolated in the proximal part) to cut pieces or chips of the prostate and to coagulate any bleeding areas. The use of these electrically operated resectoscopes has certain disadvantages. For example, there is a need for a very powerful diathermy machine; the electric loops through which the electricity runs have an average useful life of only one or two patients; each loop costs approximately fifty dollars; and the procedure produces tissue charring or carbonization which produces a slightly higher risk of a location for infection. (Charred tissue is dead tissue and with urine and blood flows close thereto, bacteria might find a suitable place to multiply.)

Furthermore, while operating time depends greatly on the size of the prostate as well as the skill of the operator, other considerations also increase operating time. These include excessive bleeding, a small bladder capacity to receive the irrigation fluid and the removal of prostatic chips. The average skilled operator or surgeon may take approximately one minute to remove each gram of prostatic tissue. Since the majority of prostate surgical removals are under 100 grams, e.g., approximately 20 to 60 grams, it can be seen that the process can become quite time consuming—and there are some prostates that range in size from 100 to 250 grams. Accordingly, it can be seen that any process or apparatus which decreases the operating time would be very beneficial.

In U.S. Pat. No. 4,955,882 (Hakky) there is disclosed a resectoscope instrument embodying a laser for use in coagulating and removing prostate tissue. A cutting blade is provided in that instrument for cutting away tissue which had been coagulated by the laser. To that end the instrument utilizes a forward directed laser to penetrate the tissue to be removed prior to cutting of that tissue. The instrument also includes means by which a irrigation fluid can be continuously supplied to and removed from the cutting site, so that the irrigation fluid, cut tissue and any debris are withdrawn through the instrument without the need to fully irrigate the bladder.

Some devices are now becoming available for effecting transurethral resection of the prostate by means of a laser. For example, Surgical Laser Technologies of Oaks PA offers a "contact laser" which serves to vaporize the prostate in order to reduce bleeding and morbidity common with the traditional transurethral resection techniques. Another laser device is offered by Intra-Sonix, Inc. of Burlington, Mass. for effecting what it refers to as "transurethral ultrasound guided laser induced prostatectomy" (TULIP). That device utilizes a laser mounted on an ultrasonic transducer introduced transurethrally to heat the prostate tissue to the point that it becomes necrotic so that it sloughs off and is expelled in the patient's urine over an extended period of time, e.g., three to six weeks, following the surgical procedure.

As should be appreciated by those skilled in the art, when performing a prostate resection (or other tissue resection procedures, for that matter) it is desirable to be able to be able to retrieve the removed tissue for analysis, e.g., histological examination. Thus, laser devices which do not include any means for effecting the retrieval of lased tissue, particularly with the cellular architecture of that tissue substantially preserved, leave much to be desired from the standpoint of patient care.

For example, the use of such devices leaves open the possibility of the failure to detect pathological conditions, e.g., malignant cells, in the removed tissue. Accordingly, the need exists for a laser resectoscope for effecting transurethral prostatectomy or other surgical procedures which addresses this concern.

A further consideration of prostate surgery is the fact that the capsule of the prostate contains many veins, and if any of these are breached, the capsule will bleed profusely and will allow the irrigation fluid to escape outside the urinary system into the area surrounding the prostate. This not only causes pain, but electrolyte disturbance with an increased morbidity and even possibly mortality. In order to avoid piercing the capsule, many surgeons stop short of the capsule by 0.5-1 mm or more depending on the skill of the operator and anatomy of the prostate. It would, of course, be beneficial to get as close to (without invading the capsule) as possible. Such skill is only obtained after many years of practice.

Thus, a need also exists for apparatus to enable the performance of prostate surgery as close to the capsule or even up to the capsule without damaging the capsule. Having such ability would not only allow much more thorough removal of the undesirable tissue, but would also reduce the anxieties associated with possible invasion of the capsule.

OBJECTS OF THE INVENTION

Accordingly, it is the general object of this invention to provide an apparatus and a method of use which overcomes the disadvantages of the prior art.

It is a further object of this invention to provide an apparatus and method of use which enables the resection of tissue by means of a laser, yet which facilitates the retrieval of lased tissue for examination thereof.

It is still a further object of this invention to provide an apparatus and method of use which increase the speed, efficiency and safety and decrease the cost of the cutting operation associated with transurethral surgery of the prostate gland and/or bladder.

It is an additional object of this invention to provide a resectoscope utilizing a laser for coagulating tissue and having a rotary cutting member for efficiently removing tissue resected so that it can be retrieved for examination with its cellular structure substantially preserved.

It is another object of this invention to provide a resectoscope which further has a laser for use in conjunction with the cutting means which penetrates the tissue to be cut and removed prior to cutting in order provide hemostasis at the site of the cutting and thereby reduce bleeding during the cutting process.

It is yet another object of the invention to provide rotatable cutting members which can be easily interchanged depending on the type of cutting to be performed.

It is still a further object of this invention to provide a resectoscope utilizing a laser for coagulating tissue, mechanically means for efficiently resecting the coagulated tissue, and irrigation and suction means for effecting the irrigation of the operative situs and the removal of the resected tissue and irrigation liquid on a continuous basis.

SUMMARY OF THE INVENTION

These and other objects of the instant invention are achieved by providing a method and apparatus for removing organic tissue from the body of a living being. In particular, the apparatus and its method of use is arranged for coagulating and causing hemostasis in tissue, e.g., prostate tissue, of a living being and for effecting the removal of the coagulated tissue. To that end the apparatus comprises an elongated member having a distal end portion for introduction, e.g., through an introducer sheath, into the being adjacent the tissue to be removed. Laser means are provided at the distal end portion of the elongated member for producing and directing a laser beam into the adjacent tissue to coagulating at least a portion of it.

A rotatable cutting means is also located at the distal end portion of the apparatus for removing at least a portion of the coagulated tissue and for carrying that removed tissue to means for retrieving it. The rotatable cutting means operates in such a manner that the cellular architecture of the coagulated tissue removed by the cutter is substantially preserved and hence suitable for viable histological examination.

In accordance with a preferred embodiment of this invention the resectoscope includes means, e.g., an irrigation lumen, for irrigating the operative situs with a liquid, e.g., saline, means, e.g., a pair of light-carrying optic fibers, for illuminating the operative situs, a viewing system, e.g., an optical fiber and associated components, so that the resection procedure can be viewed by the surgeon, e.g., via a telescope and/or video monitor, and means, e.g., a suction lumen, for carrying the irrigation liquid, blood and particles of the lased tissue out of this instrument for collection.

DESCRIPTION OF THE DRAWINGS

Other objects and many of the attendant advantages of this invention will be readily appreciated as the same becomes better understood by reference to the following detailed description when considered in connection with the accompanying drawings wherein.

DESCRIPTION OF THE PREFERRED EMBODIMENT OF THE INVENTION

Figure 1:
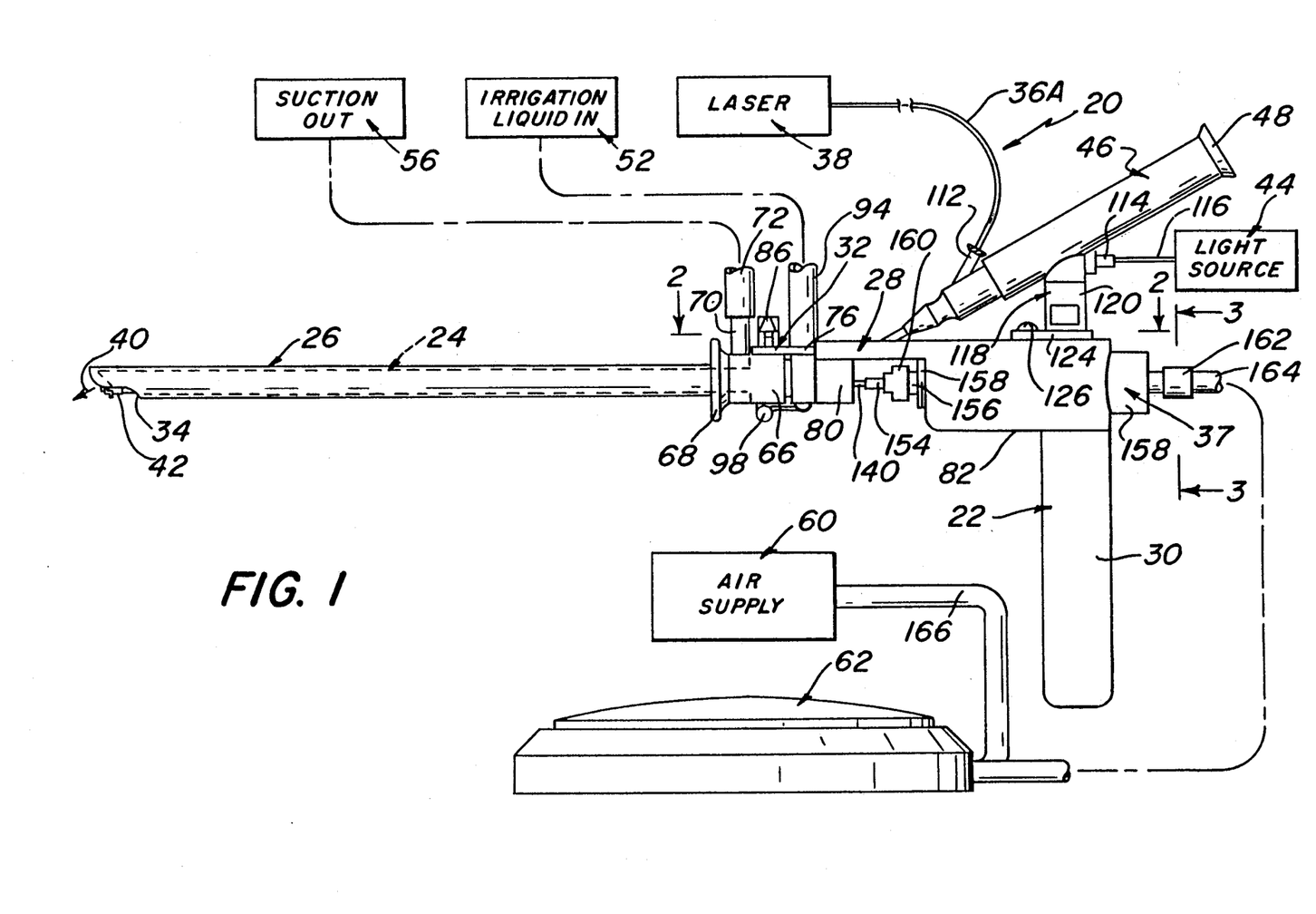
FIG. 1 is a side elevational view of the resectoscope of the present invention.

Referring now in greater detail to the various figures of the drawing wherein like reference characters refer to like parts, a resectoscope apparatus constructed in accordance with the present invention is shown at generally 20 in FIG. 1. The resectoscope is arranged to conduct the removal of internally located tissue from a patient quickly, easily, and with little pain or bleeding and by the use of a laser in conjunction with a mechanical cutter. Moreover, the resectoscope is constructed so that the tissue removed thereby is suitable for histological examination since its cellular architecture will be substantial re-preserved.

Before discussing the details of the operation of the apparatus 20 a short summary of its salient features is in order. To that end, the apparatus 20 basically comprises an instrument 22 having an elongated distal end portion 24 and a supporting frame 28. The instrument 22 is used in conjunction with a tubular sheath 26. In particular, the instrument 22 and the tubular sheath 26 are arranged to be releasably secured together to form the resectoscope apparatus 20 when it is to be operated to perform a transurethral prostatectomy or any other suitable surgical procedure. To that end a conventional obturator (not shown) may be used to effect the location of the sheath 26 within the patient's body at the desired location so that the instrument 22 can then be inserted into the sheath 26.

The instrument's frame 28 includes a downwardly extending handle 30 arranged to be grasped in the hand of the surgeon so that the instrument can be supported and manipulated by the surgeon using only a single hand.

When the apparatus 20 is used for prostrate resection the sheath 26 with the obturator (not shown) therein is introduced transurethrally until the distal end of the sheath is located adjacent to the patient's prostrate. The obturator is removed, the elonqated distal portion 24 of the instrument 22 inserted therethrough, and the instrument is secured to the sheath by a locking mechanism 32.

As can be seen clearly in FIGS. 1 and 4, the sheath includes an open distal end 34 through which the working end, e.g., the portion of the instrument for lasing and resecting the prostate tissue, of the instrument 22 is exposed to perform the various operations as will be described later.

A lumen 36 extends through the elongated portion 24 of the instrument and carries an optic fiber 36A therethrough. The fiber is provided to transmit laser light from a remote laser source 38, e.g., a YAG laser. The free end of the fiber 36A is bent downward at an acute angle, e.g., 60 degrees, to the longitudinal axis of the instrument, in the direction of arrow 40 (FIGS. 1 and 4), so that the laser light is directed therealong to exit somewhat laterally out of the distal end of the instrument and sheath into the tissue to be removed, e.g., through the urethra and into the prostate (in the case of a transurethral prostatectomy). The laser light penetrates several millimeters, e.g., 1 to 3 mm, into the tissue to heat it, whereupon the tissue is coagulated. This action results in almost instantaneous hemostasis of that tissue and reduces, if not eliminates, bleeding thereat.

In accordance with the preferred aspect of this invention the coagulated tissue is removed from the remaining tissue by means of a rotatable cutting member 42. That member is mounted at the distal end of the instrument 22 and preferably comprises a pair of planar blades (to be described later). The blades are arranged to be rotated at a high rate of speed about their axis of rotation, i.e., an axis which is parallel to the longitudinal of the instrument, via transmission assembly (to be described later) coupled to a pneumatically operated motor 37. The motor 37 is mounted on the frame 28 adjacent the handle 30.

The instrument 22 also includes the means for effecting the illumination and visualization of the operative field while the instrument is in use. That means basically comprises a pair of optic fibers 36B and 36C, also extending through the lumen 36. These fibers carry light from an external light source 44 through the instrument and out their distal ends so that the light exiting therefrom illuminates the operative field or situs to the front and somewhat to the sides of the distal end of the device. Another optic fiber or bundle of fibers 36D also extends through the lumen 36 for carrying the image of the operative field to a conventional telescope 44 mounted on the instrument's frame 28. This allows the surgeon to visually observe the resection procedure. The visual image is also preferably conveyed to some other optical viewing means, e.g., a video monitor (not shown) by mounting a camera (not shown) on to the telescope's eye piece 48. The distal end of the optic fiber 36D includes a lens (not shown) which directs the field of view of the fiber downward from the longitudinal axis at approximately 60 degrees.

In order to facilitate the resection operation, the elongated portion 24 of the instrument 22 includes a conduit or lumen 50 (FIGS. 5 and 6) through which an irrigation liquid, e.g., saline, from a source 52 is carried and directed out the distal end of the instrument toward the situs of the tissue to be removed. This action clears the area of blood and tissue particles produced by the operation of the apparatus (as will be described later), thereby expediting the surgeon's visualization of the operative situs. Moreover, the introduced liquid serves as a means for carrying the coagulated tissue which is cut away by the rotating blades out of the instrument for retrieval and subsequent histological examination. To that end, the space between the tubular sheath 26 and the outer periphery of the components making up the elongated portion 24 of the instrument 22 form a lumen 54 through which the irrigation fluid and cut tissue can be withdrawn by suction. In particular, the lumen 54 is coupled to a remote vacuum source 56.

Air for powering the motor 37 to rotate the blades is provided from a air supply 60 via a foot control pedal 62. This construction enables the operation of the air motor to be controlled by the surgeon by merely pressing his/her foot on the pedal while holdinq the instrument in his/her hand, thereby freeing the surgeon's other hand for other activities.

In accordance with one preferred aspect of this invention, the blades forming the rotating cutter 42 are constructed and configured to cut the coagulated tissue away from the remaining tissue after it has been lased so that removed tissue can be retrieved in pieces of sufficient size and with their cellular architecture substantially intact so that they are suitable for subsequent histological examination. Moreover, it is desirable that the operation of the blades direct the cut tissue into the suction lumen 54 so that virtually all of it may be removed from the patient's body. One particular suitable arrangement to achieve those ends is to have the blades oriented at a small acute angle, e.g., five degrees, to the axis of rotation.

Figures 2, 3, 7, 8:
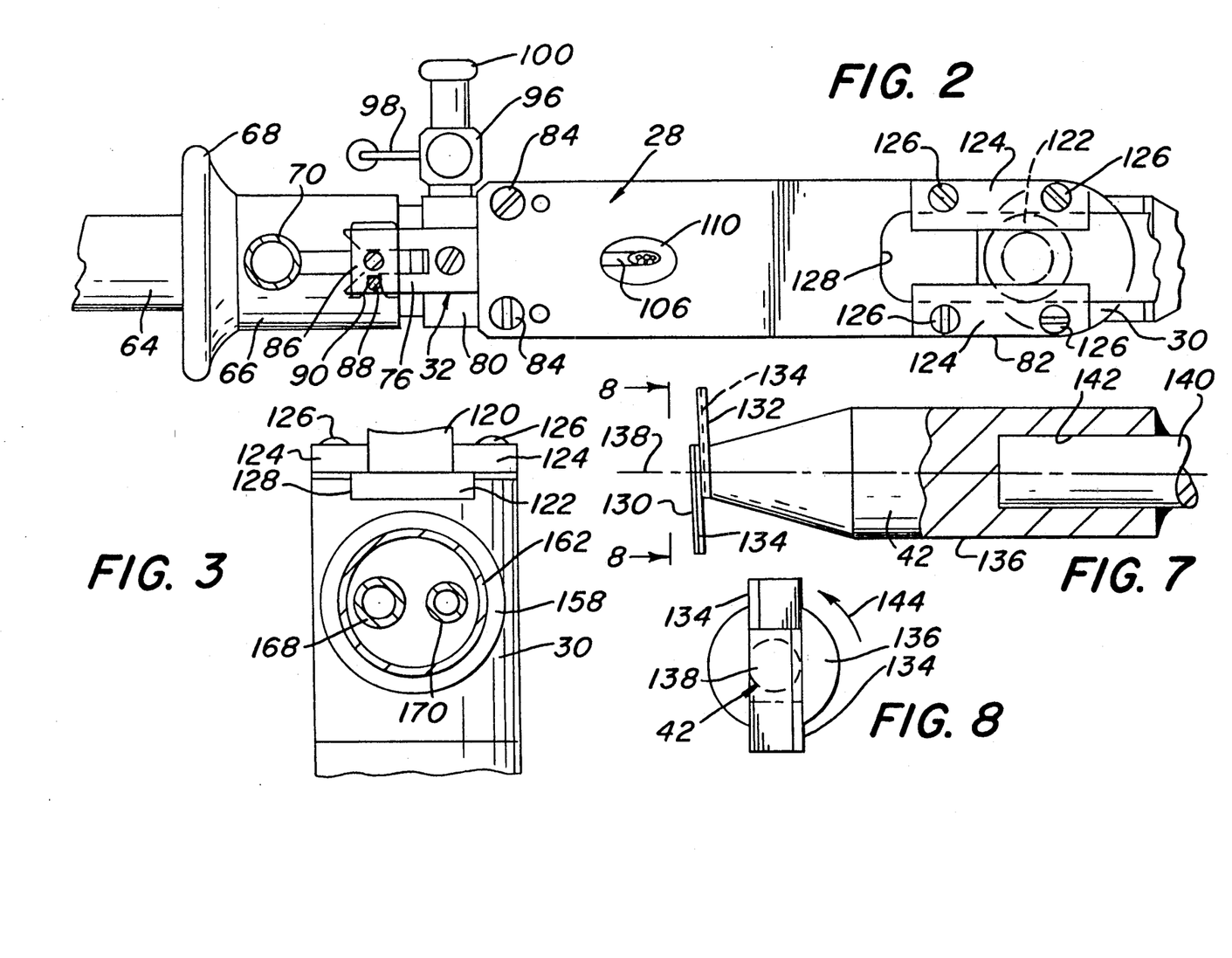
FIG. 2 is an enlarged sectional view taken along the line 2—2 of FIG. 1.
FIG. 3 is an enlarged sectional view taken along the line 3—3 of FIG. 1.
FIG. 7 is a greatly enlarged side elevational view, partially in section, of the cutter of the resectoscope shown in FIG. 1.
FIG. 8 is an end view of the cutter taken along the line 8—8 of FIG. 7.
Figure 4:
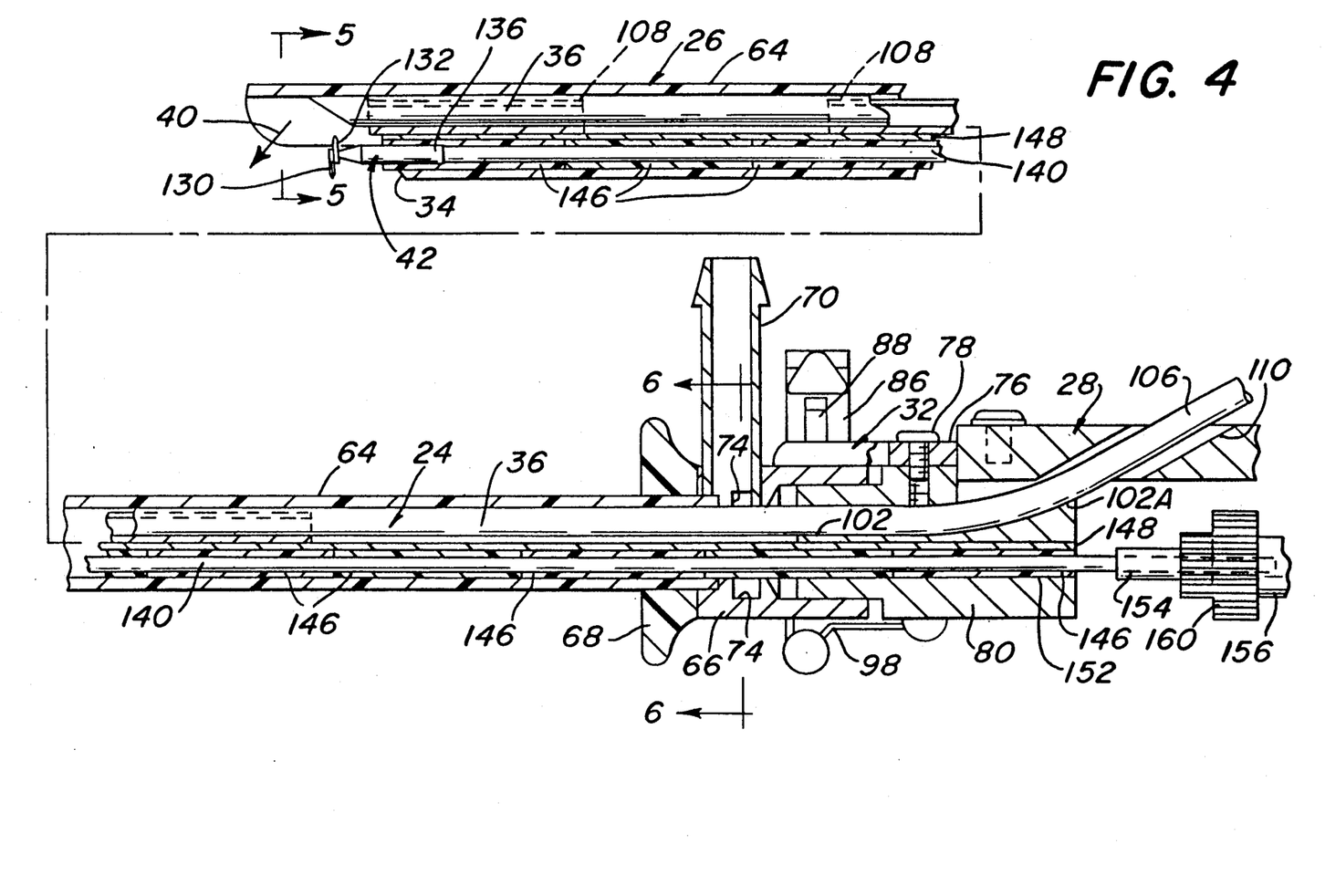
FIG. 4 is an enlarged longitudinal section view of the distal end of the resectoscope shown in FIG. 1.

Referring now to FIGS. 1, 2, and 4 the details of the tubular sheath 26 will now be considered. As can be seen therein, the sheath 26 basically comprises a hollow tube 64, preferably formed of fiber glass, plastic, or stainless steel, and approximately eight inches (20.3 cm) long. At the proximal end of the tube 64 is a base member or collar 66 having a peripheral lip 68 extending from the distal side thereof. The base member 66 is hollow and is coaxially aligned and fixedly secured to the tube 64. The collar includes a central passageway or bore in which the elongated portion 24 of the instrument extends. A coupling 70 extends radially out of the collar 66. The coupling 70 is hollow and includes a lip 72 at its free end for securement to a flexible suction line or conduit 72. The suction line 72 is connected to the vacuum source 56. An annular recess 74 is provided in the inner peripheral of the collar 66 communicating with the hollow interior of the coupling 70. The recess 74 communicates with the suction lumen 56 as clearly seen in FIG. 6.

The locking mechanism 32 includes a portion mounted on the collar 66 and a portion mounted on the frame 28 to releasably secure the two together. The obturator also preferably includes a component to cooperate with the component on the collar 66 to releasably secure the obturator to the tubular sheath when the obturator is used with the sheath to introduce it transurethrally. The details of the locking mechanism 32 can be best seen in FIGS. 2 and 4. Thus, as can be seen therein, the mechanism 32 basically comprises a yoke member 76 mounted via a screw 78 onto a mounting block 80. The block 80 is, in turn, secured to a housing 82 of the frame 28 via plural screws 84. The heretofore identified handle 30 is mounted at the bottom of the housing portion 82. An upstanding, biased catch or wing nut 86 is fixedly secured to the top of the collar 66 and is arranged to be twisted to be releasably secured within the yoke 76. A locking pin 88 projects upward from the yoke 78 for receipt in a slot 90 in the catch 86 when the catch is in place within the yoke.

As mentioned earlier, the distal end 34 of the tubular sheath 26 is open. In particular, the distal end of the tube 64 includes a cut-away portion which opens approximately 180 degrees of the circumference of the tube 64 at the bottom side of the distal end thereof, while the top of the distal end of that tube remains covered. The covered portion of the distal end of the sheath serves to shield a portion of the operative situs from the emerging laser beam and the rotating cutter blades.

Referring now to FIGS. 1, 2, 5, and 6 the details of the system for irrigating the operative site or field will be described. That system basically comprises the heretofore identified irrigation liquid supply 52 and the conduit or lumen 50, as well as a flexible conduit or tube 94 and a control valve 96.

The control valve 96 is basically an on/off valve of any conventional construction and includes a pivotable actuating lever 98. The valve 96 is fixedly mounted on the mounting block 80 of the instrument's frame. A controllable passageway (not shown) is located in the valve and communicates with a transverse bore (not shown) in the interior of the block 80. The lumen 50 basically comprises of an elongated, rigid tube, having a proximal end portion fixedly mounted within a longitudinally extending bore (not shown) within the block 80. An opening (not shown) is provided in the proximal end of the lumen 50 communicating with the transverse bore in the block 80 and hence with the controllable passageway in the valve 96. The input to the control valve 96 is in the form of a coupling 100, which is arranged to be received within the end of the irrigation fluid carrying conduit 94.

The valve 96 is arranged, when opened, to enable irrigation liquid, e.g., saline, from the source 52 and the conduit 94 to flow through it and the communicating bores and openings into the proximal end of the lumen 50, from whence it flows down that lumen. The distal end of the lumen 50 is located immediately adjacent the cutting member 42 and is open. Thus, the irrigation liquid exits from the instrument adjacent the cutting member 42.

The opening and closing of the valve 96 is accomplished by pivoting its actuating lever to the desired position.

As mentioned earlier, the lumen 36 is arranged to carry the optic fibers bearing the laser light, the illumination light, and the image of the surgical field. In particular, the lumen 36 basically comprises a rigid, e.g., aluminum, elongated tube extending the length of the distal portion 24 of the instrument 22. The tube extends from a longitudinal bore 102 within the block 80 to a point immediately above the cutter 42 (see FIG. 4). A slot 104 is provided in the top of the lumen 36 and extends substantially the entire length thereof. The fibers 36A, 36B, 36C, and 36D are disposed parallel to one another in a flexible, e.g., rubber, cable 106 extending through the lumen 36. The cable 106 is held in position within the lumen 36 by plural arcuate spacers 108.

Figure 5:
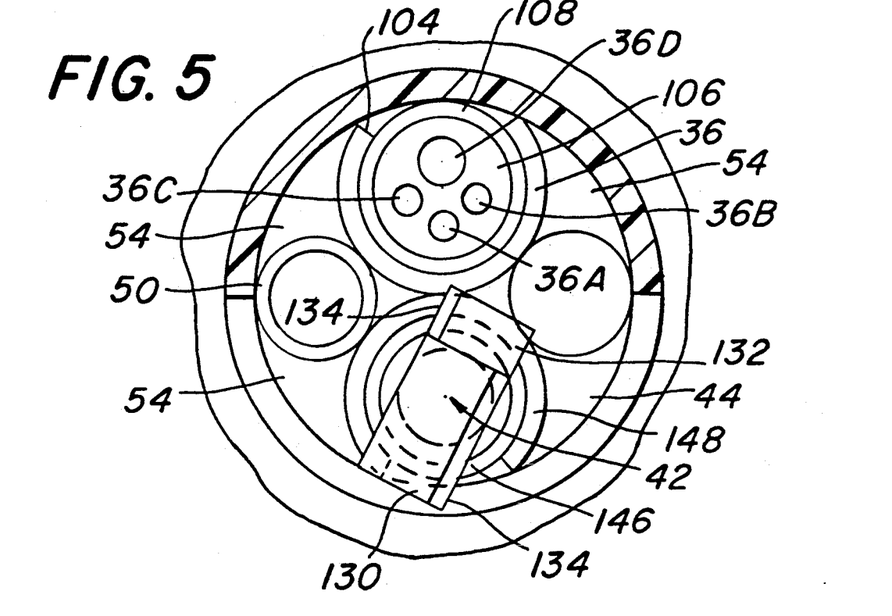
FIG. 5 is an enlarged sectional view taken along the line 5—5 of FIG. 4.

As can be seen in FIG. 5, the fibers 36B and 36C bearing the illumination light are located laterally of each other and on either side and somewhat below the central axis of the cable 106. The fiber 36D carrying the image of the surgical field back to the telescope is located above an equally spaced from the fibers 36B and 36C. The fiber 36A carrying the laser light from the laser source is located directly below the fiber 36D.

As can be seen clearly in FIG. 4 the proximal end of the cable 106 extends through an arcuate portion 102A of the bore 102 in the block 80, through an angled passageway 110 in the frame 28, into the telescope 46. The optic fiber 36A bearing the laser light extends through an angled port or luer 112 located at the front of the telescope to the laser source 38.

In accordance with the preferred embodiment of this invention the telescope 46 is a conventional device, such as an endoscope sold by Electro-Fiber Optics Corporation. The optic fiber 36D bearing the image of the operative field is brought into the telescope 46 so that image carried thereby can be seen by the surgeon looking into eye piece 48 or can be displayed on the video monitor (not shown). The proximal end of the fibers 36B and 36C terminate in a conventional (ACMI) light fitting 114 which is arranged to be coupled to a cable 116 bearing light from the light source 44.

The telescope 46 is mounted on to the frame 28 so that it can be positioned at a desired location therealong. To that end, a bracket assembly 118 is provided mounted on the housing 82 of the frame 28. The bracket assembly 118 basically comprises a standoff 120 fixedly secured to the under side of the telescope 46. The standoff includes a tongue 122 at the bottom end thereof and which is located between a pair of spaced rails 124. The rails are fixedly secured by screws 126 on to the top surface of the housing 82 over the handle 30. A slot 128 is provided in the top of the housing over the handle, with the rails 124 being disposed on opposite sides of the slot and slightly over hanging it. The standoff 120 is disposed so that its tongue 122 is within the slot 128 and is held in place by the rails 124.

As will be appreciated by those skilled in the art when the screws are loosened the standoff can be slid longitudinally within the slot 128 as guided by the rails to locate it at desired position with respect to the instrument's frame. The telescope can then fixed in place by tightening the screws 126.

The laser 38 is of any conventional construction, such as a YAG laser, sold by Laser Scope, Inc. under the model designation KTP/532.

Attention will now be directed to FIGS. 4, 5, 7, and 8 wherein the details of the cutter member 42 are shown. As can be seen therein, the cutter 42 comprises a pair of blades 130 and 132. Each blade is a thin, generally planar, rectangle member, e.g., 0.04 inch (1.02 mm) wide by 0.01 inch (0.254 mm) long, by 0.005 inch (0.13 mm) thick. The blades are formed of any suitable material, e.g., stainless steel, and each includes a leading cutting edge 134. The blades are mounted, e.g., welded, on the tapered distal end of a hub or shank 136 so that their longitudinal axes are diametrically opposed. In particular, the inner portion of the blade 130 is disposed over the inner portion of the blade 132 on the end of the shank 136 so that cutting edges 134 of the blades are not co-planar, i.e., they are spaced slightly from each other. The blades are mounted so that each lies in a plane which extends a small acute angle, e.g., five degrees, to the axis of rotation 138 of the cutter 42.

The cutter's shank 136 is fixedly secured to the end of a flexible drive cable 140 forming a portion of the transmission assembly. In particular, the distal end of the cable 140 is located and secured, e.g., welded, within a central bore 142 in the proximal end of the shank 136.

As will be appreciated by those skilled in the art when the cutter 42 is rotated about axis 138 in the direction of arrow 144 in FIG. 8, the angled blades 130 and 132 will pull and direct liquid, e.g., the saline and blood, and particles of the lased tissue cut, in the proximal direction towards the suction lumen 54. This action is of considerable importance to draw the resected tissue into the suction lumen 54 where they are carried with the irrigation fluid out of the instrument 22 for retrieval, e.g., entrapment in a filter or sieve, and subsequent histological examination.

As can be seen in FIG. 2 the drive cable 140 extends through a plurality of sequentially located tubular bushings. The bushings are preferably formed of polytetrafluoroethylene (TEFLON) and are, in turn, held within an elongated rigid sleeve 148. The sleeve 148 extends down the entire distal end portion 24 of the instrument 22 and includes a longitudinally extending slot 150 along its bottom surface. The proximal end of the sleeve 148 is located within a bore 152 extending longitudinally through the block 80 and is fixedly secured in place therein.

The proximal end of the drive cable 140 is arranged to be located and secured within a split bushing 154 mounted on the drive shaft 156 of the air motor 37. The motor 37 is mounted within the housing 82 over the handle 30. The proximal end 158 of the air motor extends out of an opening in the proximal end of the housing 82. A knurled tightening collar 160 is mounted on the output shaft 156 and extends over the split bushing 154. Thus, when tightening the collar squeezes the bushing 154 into tight engagement with the proximal end of the drive cable 140 to secure the cable to the output shaft 156 of the motor. The proximal end of the motor includes a coupling 162 for connection to an air line 164. The other end of the air line 164 is connected to the foot switch 62. When so connected air from the supply 60 is provided, via a flexible conduit 166, to the foot switch 62, and from there through the line 164 and coupling 162 to the air motor 37. This action cause the air motor to operate to rotate its output drive shaft at a high rate of speed, e.g., 10,000 to 50,000 RPM. Accordingly, the drive cable, with the cutter attached thereto, is rotated about the axis 138 at that speed when the motor 37 is operated.

In accordance with the preferred embodiment of the invention, the air motor 158 is a conventional air driven motor, such as that sold my Micro-Motors, Inc., under model designation MMD-1000X. The foot switch 62 is also of conventional construction, such as that sold by Micro-Motors, Inc. under model designation 2846.

As can be seen in FIG. 3, the coupling 162 includes a conduit 168 therein which is arranged to be connected to the air provided from the supply 60 via the foot switch 62 to cause the motor 37 to commence rotation. The coupling 162 also includes a outlet toward 170 to enable air from the motor to exit therefrom.

Figure 6:
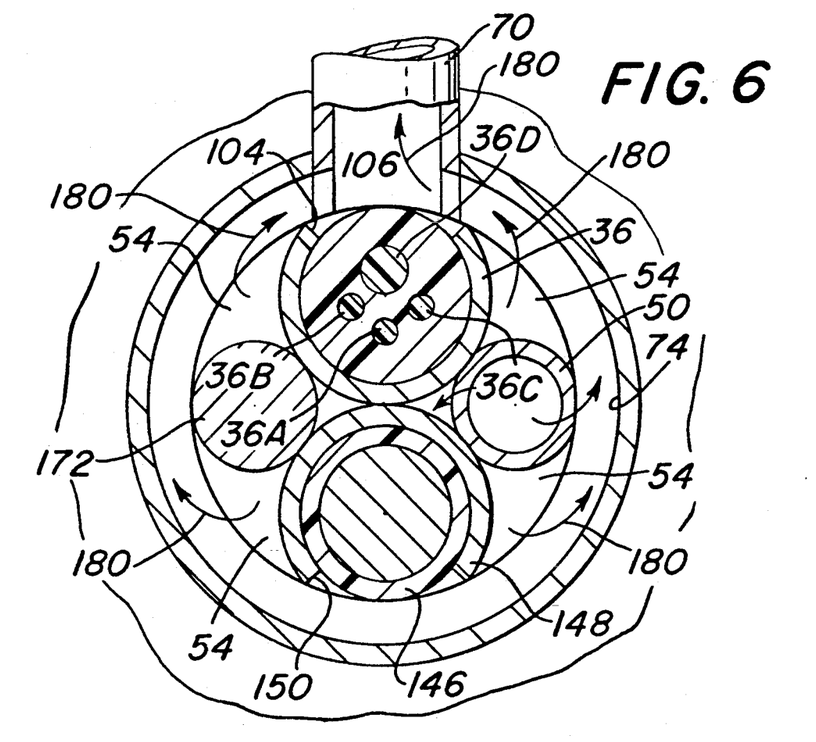
FIG. 6 is an enlarged sectional view taken along the line 6—6 of FIG. 4.

As can be seen in FIG. 6, a rod 172 of the same outside diameter as that of the lumen 50 is mounted along the distally extending portion 24 of the instrument 22 and diametrically opposite the lumen 50. The rod 172 serves to balance the instrument, i.e., render the suction lumen 54 symmetrical.

As mentioned earlier, the eye piece 48 of the telescope 46 is arranged to have a camera mounted thereon so that the image of the field within the patient's body can be displayed on a video monitor (not shown). Preferably that monitor is also connected to a color analyzer (not shown) which is capable of analyzing the color of the tissue as it is being removed. It has been found that the color of the tissue is a function of the depth and health of the tissue. By carefully monitoring the color it is possible to adjust the power (wattage) of the laser according to the type of tissue being lased. Moreover, one or more computers (not shown) can be used to provide automated analysis of the color is connection with the laser control to effect the automatic adjustment of the range of laser wattage to be lower, e.g., 10 watts, for healthier cells (red) and higher (e.g., 45 watts) for dead cells (white). Red tissue indicates the presence of blood and represents health tissue, while whiter tissue indicates the absence of blood and generally means the cells are dead or dying.

In accordance with the preferred embodiment of the invention, the irrigation and suction are operated at the same time so that the irrigation fluid along with blood and cut tissue particles are directed into the distal end of the suction lumen 54 and carried proximally therethrough and out of the instrument. This eliminates the need to store the irrigation of fluid and tissue particles in the bladder until the bladder can be evacuated. This ability to provide continuous irrigation liquid to the situs of the tissue to be resected via the irrigation lumen 50, the continuous withdrawal of the irrigation fluid, blood, and cut tissue particles through the suction conduit 54 also improves visibility.

In accordance with one aspect of the invention, pressure sensing equipment (not shown) may be provided in conjunction with the fluid irrigation and evacuation system. The pressure sensing equipment can be used to sense the back pressure of the fluid at the situs of the tissue to be removed to control the irrigation liquid flow into and out the operative situs in order to prevent excessive or insufficient fluid in that area, thereby preventing unnecessary fluid flow or drainage to tissues.

Operation of the apparatus 20 to effect a transurethral prostrate resection is as follows: the tubular sheath 26 is introduced through the urethra toward the prostrate to the desired location. If desired, an obturator may be used to effect the safe positioning of the tubular sheath 26. The obturator is then removed and the instrument is connected to the tubular sheath. To that end, the elongated distal portion 24 of the instrument 22 is inserted into the proximal end of the sheath 26 and slid down until the working or distal end of the instrument 22 is located at the open end 34 of the sheath. The instrument and the sheath are then locked together by the latch mechanism 32 to prevent relative movement therebetween.

The light source 44 is then actuated to cause the operative field to be illuminated by the light emanating from the distal ends of the optical fibers 36B and 36C. At this point, the irrigation liquid is introduced into the instrument by opening the valve 96. The irrigation liquid, e.g., saline, thus flows down the lumen 50 and exits from the distal end thereof as noted earlier. This irrigates and clear the area being resected. The laser may then be operated to project the laser beam sideways, i.e., in the direction of arrow 40, so that it penetrates the tissue in front of the cutter 42. The side projected laser beam penetrates the tissue to a depth of a few millimeters, thereby coagulating that tissue and causing its immediate homeostasis, as described earlier.

Once the tissue has been lased sufficiently the surgeon may depress the foot pedal 62 to commence operation of the cutter. The lased tissue may then be cut away by the surgeon by moving the instrument to urge the rotating cutter blades against the lased tissue. The angled blades cut away particles of the lased tissue and direct those particles along with blood and irrigation liquid into the suction lumen 54. Those materials flow proximately through the suction lumen and out through the port 70 in the direction of arrows 180 in FIG. 6. From the port 70 they flow through the coupled conduit 72 to the means 56 where the tissue particles can be collected for subsequent histological examination. In this regard as mentioned earlier the instrument 22 of this invention operates to lase and removed tissue without destroying the cellular architecture of the tissue to the degree at which a viable histolotical analysis can not be achieved.

It should be pointed out that the operation of the laser in coagulating the lased tissue will result in some of the tissue being sloughed off immediately. Such tissue can be retrieved in the same manner as described heretofore without necessitating the operation of the cutter 42. However, all coagulated prostate tissue which has not been sloughed off can be removed by operation of the cutter, if desired by the surgeon.

The rotating cutter and its associated drive cable can be removed from the instrument by unscrewing the knurled sleeve to release the split bushing. A new blade and associated drive cable can then be mounted in the instrument, when such action is desired.

In a test of the resectoscope 20, like that described above, a transurethral prostatectomy was accomplished wherein the laser source 38 was operated to provide between 40 and 60 watts of power. The prostrate tissue was lased for three to five seconds. Subsequent and synchronized action of the rotating cutter blades resected the prostate tissue effectively, so that all of the lased tissue was pushed toward suction lumen. Normal saline was used for irrigation. The suction lumen 72 was coupled to a sieve (not shown) to collect the removed tissue. The largest prostatic tissue removed by the operation of the resectoscope was approximately 2 millimeters in diameter, with the amount of resection being accomplished at a rate of approximately six to eight grams per minute. The retrieved prostrate tissue was fixed using a 10 percent formula, and was mounted on sides, stained, and examined in the standard fashion. Complete preservation of the cellular architecture was noted permitted normal histological examination.

Without further elaboration, the foregoing will so fully illustrate our invention that others may, by applying current or future knowledge, readily adopt the same for use under various conditions of service.

We claim:

1. A surgical apparatus for coagulating and removing tissue of a living being, said apparatus being an elongated member having a distal end portion for introduction into said being adjacent said tissue, laser directing means located at said distal end portion directing a laser beam from laser beam producing means coupled to said apparatus into said tissue for coagulating a portion of said tissue while preserving the cellular architecture thereof, thin planar rotatable cutting blade means located at said distal end portion for removing at least a portion of said coagulated tissue by cutting away particles of said portion of said coagulated tissue, and conduit means coupled to said rotatable cutting means for carrying said particles to means for retrieving said particles, said rotatable cutting means being operable to engage and cut said coagulated tissue to produce said particles, with the cellular architecture of said retrieved particles being sufficiently preserved for histological examination.

2. The apparatus of claim 1 for performing a prostatectomy on a living person, wherein said elongated portion is configured for transurethral introduction to a position adjacent the prostate of said living person.

3. The apparatus of claim 2 wherein said cutting blade means comprises at least one substantially planar cutting blade, said blade being mounted at a small acute angle to an axis about which said blade is rotated.

4. The apparatus of claim 2 additionally comprising drive means for rotating said cutting blade means wherein said cutting blade means is rotated by said drive means within the range of 10,000 to 50,000 RPM.

5. The apparatus of claim 2 additionally comprising suction means to aid in the removal of said tissue.

6. The apparatus of claim 5 additionally comprising means for providing an irrigation liquid to said distal end of said apparatus.

7. The apparatus of claim 2 additionally comprising means for providing an visual image of the tissue of the prostate as said laser beam is directed to said tissue to coagulate said tissue and said cutting means is operated to removed said particles from said coagulated tissue.

8. The apparatus of claim 1 wherein said cutting blade means comprises at least one substantially planar cutting blade, said blade being mounted at a small acute angle to an axis about which said blade is rotated.

9. The apparatus of claim 8 wherein said small acute angle is approximately 5 degrees.

10. The apparatus of claim 1 wherein said cutting blade means comprises a pair of substantially planar cutting blades, each of said blades being mounted at a small acute angle to an axis about which said blade is rotated.

11. The apparatus of claim 10 wherein said small acute angle is approximately 5 degrees.

12. The apparatus of claim 11 wherein said blades are slightly offset from each other.

13. The apparatus of claim 10 wherein said blades are slightly offset from each other.

14. The apparatus of claim 1 additionally comprising drive means for rotating said cutting blade means wherein said cutting means is rotated by said drive means within the range of 10,000 to 50,000 RPM.

15. The apparatus of claim 1 additionally comprising suction means to aid in the removal of said tissue.

16. The apparatus of claim 15 wherein said suction means comprises a lumen having an opening at said distal end portion of said apparatus.

17. The apparatus of claim 16 wherein said suction means comprises a lumen having an opening at said distal end portion of said apparatus.

18. The apparatus of claim 1 additionally comprising means for providing an irrigation liquid to said distal end of said apparatus.

19. The apparatus of claim 1 wherein said apparatus additionally comprises a tubular sheath, and wherein said elongated member comprises a portion of a device suitable to be supported by hand, said tubular sheath having an open distal end insertable into the body of said being adjacent said tissue, said device including releasably securable means to releasably secure said device within said tubular sheath.

20. The apparatus of claim 19 wherein said device additionally comprises suction means extending through said elongated portion thereof of aid in the removal of said tissue.

21. The apparatus of claim 20 wherein said suction means comprises a lumen having an opening adjacent said open distal end of said tubular sheath.

22. The apparatus of claim 21 wherein said lumen is formed by a space between said tubular sheath and said elongated portion of said device.

23. The apparatus of claim 22 wherein said device additionally comprising means for providing an irrigation liquid to said open distal end of said tubular sheath.

24. The apparatus of claim 23 wherein said last mentioned means comprises a lumen extending through said elongated portion of said device and having an open end located adjacent said open distal end of said tubular sheath.

25. The apparatus of claim 24 additionally comprising imaging means for providing an visual image of the tissue as said laser and said cutting means is operated, said imaging means comprising optic fiber means extending through said elongated portion of said device.

26. The apparatus of claim 25 wherein said device comprises motor means to effect the rotation of said cutting means.

27. The apparatus of claim 19 wherein said device additionally comprising irrigation means for providing an irrigation liquid to said open distal end of said tubular sheath.

28. The apparatus of claim 27 wherein said irrigation means comprises a lumen extending through said elongated portion of said device and having an open end located adjacent said open distal end of said tubular sheath.

29. The apparatus of claim 19 additionally comprising imaging means for providing an visual image of the tissue as said laser and said cutting means is operated, said imaging means comprising optic fiber means extending through said elongated portion of said device.

30. The apparatus of claim 29 wherein said device comprises motor means to effect the rotation of said cutting means.

31. The apparatus of claim 1 additionally comprising means for providing an visual image of the tissue as said laser and said cutting means is operated.

32. A method of coagulating and removing tissue of a living being, said method comprising the steps of introducing elongated means having a distal end portion into the body of said being to a position adjacent said tissue, coupling laser beam producing means to said distal end portion of said elongated means, directing a laser beam from said laser beam producing means into said tissue adjacent said distal end portion of said elongated means to coagulate at least a portion thereof, providing rotatable cutting means located at said distal end portion for engaging and cutting at least a portion of said coagulated tissue to create particles thereof, with the cellular architecture of said particles being sufficiently preserved for histological examination, and carrying said particles out of the body of said being through said elongated means for retrieval.

33. The method of claim 32 additionally comprising performing a histological examination on said retrieved tissue.

34. The method of claim 33 wherein said method comprises removing at least a portion of the prostate of a living being, and wherein said distal end of said elongated means is introduced transurethrally to a position adjacent said prostate.

35. The method of claim 33 wherein said tissue is removed at the rate of approximately 6 to 8 grams per minute.

36. The method of claim 35 wherein said method comprises removing at least a portion of the prostate of a living being, wherein said laser beam is provided by a YAG laser operating within the range of 40–60 watts, and wherein said prostate tissue is lased for a period of 3 to 5 seconds.

37. The method of claim 36 wherein said laser beam penetrates said tissue to a depth approximately one to three millimeters.

38. The method of claim 33 wherein said laser beam penetrates said tissue to a depth approximately one to three millimeters.

39. The method of claim 33 additionally comprising the step of irrigating the situs of said prostate tissue to be removed with a liquid, and causing said liquid to carrying said portions of said coagulated prostate tissue removed by said cutting means away from said situs for retrieval thereof.

40. The method of claim 32 wherein said method comprises removing at least a portion of the prostate of a living being, and wherein said distal end of said elongated means is introduced transurethrally to a position adjacent said prostate.

41. The method of claim 32 additionally comprising applying suction to said removed tissue aid in the retrieval thereof.

42. The method off claim 41 additionally comprising providing an irrigation liquid to said tissue.

43. The method of claim 32 additionally comprising providing an irrigation liquid to said tissue.

44. The method of claim 32 wherein said rotatable cutting means is rotated at a speed in the range of 10,000 to 50,000 RPM.

45. The method of claim 32 wherein said method comprises removing at least a portion of the prostate of a living being, wherein said laser beam is provided by a YAG laser operating within the range of 40–60 watts, and wherein said prostate tissue is lased for a period of 3 to 5 seconds.

46. The method of claim 32 wherein said laser beam penetrates said tissue to a depth approximately one to three millimeters.

47. The method of claim 32 further comprising inserting a tubular sheath into said being to the situs of tissue to be removed, inserting said elongated means into said sheath in such a manner that a portion of said sheath shields a lateral portion of said rotatable cutting means, while another lateral portion of said cutting means is exposed.

48. The method of claim 32 additionally comprising the step of irrigating the situs of said tissue to be removed with a liquid, and causing said liquid to carrying said portions of said coagulated tissue removed by said cutting means away from said situs for retrieval thereof.

* * * * *